United States Patent
Kruspe et al.

(10) Patent No.: US 7,268,547 B2
(45) Date of Patent: Sep. 11, 2007

(54) CORRECTION OF MOTION INFLUENCES IN NMR SIGNALS

(75) Inventors: Thomas Kruspe, Celle (DE); Martin Blanz, Celle (DE)

(73) Assignee: Baker Hughes Incorporated, Houston, TX (US)

(*) Notice: Subject to any disclaimer, the term of this patent is extended or adjusted under 35 U.S.C. 154(b) by 34 days.

(21) Appl. No.: 10/958,608

(22) Filed: Oct. 5, 2004

(65) Prior Publication Data

US 2005/0088176 A1 Apr. 28, 2005

Related U.S. Application Data

(60) Provisional application No. 60/509,421, filed on Oct. 7, 2003.

(51) Int. Cl.
*G01V 3/00* (2006.01)

(52) U.S. Cl. ........................ 324/303; 324/306

(58) Field of Classification Search ............... 324/303, 324/306
See application file for complete search history.

(56) References Cited

U.S. PATENT DOCUMENTS

| | | | |
|---|---|---|---|
| 5,389,877 A | 2/1995 | Sezginer et al. | 324/303 |
| 5,705,927 A | 1/1998 | Sezginer et al. | 324/303 |
| 6,268,726 B1 | 7/2001 | Prammer et al. | 324/303 |
| 6,297,632 B1 | 10/2001 | Speier | 324/303 |
| 6,437,564 B1* | 8/2002 | Itskovich et al. | 324/303 |
| 6,459,263 B2 | 10/2002 | Hawkes et al. | 324/303 |
| 6,566,874 B1 | 5/2003 | Speier et al. | 324/303 |
| 6,583,621 B2* | 6/2003 | Prammer et al. | 324/303 |
| 6,825,659 B2* | 11/2004 | Prammer et al. | 324/303 |
| 6,844,728 B2 | 1/2005 | Speier et al. | 324/303 |
| 2001/0043066 A1 | 11/2001 | Hawkes et al. | 324/303 |
| 2002/0153888 A1 | 10/2002 | Kruspe et al. | 324/303 |
| 2003/0132749 A1 | 7/2003 | Speier et al. | 324/303 |
| 2003/0141869 A1 | 7/2003 | Prammer | 324/303 |

FOREIGN PATENT DOCUMENTS

| | | |
|---|---|---|
| EP | 0977057 | 11/2002 |
| GB | 2359632 | 8/2001 |
| WO | WO99/36801 | 7/1999 |
| WO | WO03/016953 | 2/2003 |
| WO | WO2005/036208 | 4/2005 |

* cited by examiner

*Primary Examiner*—Louis M. Arana
(74) *Attorney, Agent, or Firm*—Madan, Mossman & Sriram, P.C.

(57) ABSTRACT

An apparatus and method for compensating for the effect of tool motion in NMR MWD measurements. Signals obtained from a directionally sensitive receiver are compensated for the effects of tool motion. In an alternative embodiment, directional transmitters and receivers are used, with the pulsing of the transmitter controlled by the output of motion sensors. In another embodiment, the transmitters and receivers may be axisymmetric and the received signals are corrected using results of a NMR simulation program that takes account of the recorded motion of the apparatus.

63 Claims, 7 Drawing Sheets

CORRECTION OF MOTION INFLUENCES IN NMR SIGNALS

CROSS REFERENCES TO RELATED APPLICATIONS

This application claims priority from U.S. Provisional Patent Application Ser. No. 60/509,421 filed on Oct. 7, 2003.

BACKGROUND OF THE INVENTION

1. Field of the Invention

This invention relates generally to determining geological properties of subsurface formations using Nuclear Magnetic Resonance ("NMR") methods for logging wellbores, particularly for correcting for the effects of tool motions on NMR signals.

2. Background of the Art

A variety of techniques are utilized in determining the presence and estimation of quantities of hydrocarbons (oil and gas) in earth formations. These methods are designed to determine formation parameters, including among other things, the resistivity, porosity and permeability of the rock formation surrounding the wellbore drilled for recovering the hydrocarbons. Typically, the tools designed to provide the desired information are used to log the wellbore. Much of the logging is done after the well bores have been drilled. More recently, wellbores have been logged while drilling, which is referred to as measurement-while-drilling (MWD) or logging-while-drilling (LWD).

One commonly used technique involves utilizing Nuclear Magnetic Resonance (NMR) logging tools and methods for determining, among other things, porosity, hydrocarbon saturation and permeability of the rock formations. The NMR logging tools are utilized to excite the nuclei of the liquids in the geological formations surrounding the wellbore so that certain parameters such as nuclear spin density, longitudinal relaxation time (generally referred to in the art as $T_1$) and transverse relaxation time (generally referred to as $T_2$) of the geological formations can be measured. From such measurements, porosity, permeability and hydrocarbon saturation are determined, which provides valuable information about the make-up of the geological formations and the amount of extractable hydrocarbons.

The NMR tools generate a near uniform static magnetic field in a region of interest surrounding the wellbore. NMR is based on the fact that the nuclei of many elements have angular momentum (spin) and a magnetic moment. The nuclei have a characteristic Larmor resonant frequency related to the magnitude of the magnetic field in their locality. Over time the nuclear spins align themselves along an externally applied static magnetic field creating a net magnetization. This equilibrium situation can be disturbed by a pulse of an oscillating magnetic field, which tips the spins with resonant frequency within the bandwidth of the oscillating magnetic field away from the static field direction. The angle θ through which the spins exactly on resonance are tipped is given by the equation:

$$\theta = \gamma B_1 t_p / 2 \quad (1)$$

where γ is the gyromagnetic ratio, $B_1$ is the effective field strength of the oscillating field and $t_p$ is the duration of the RF pulse).

After tipping, the spins precess around the static field at a particular frequency known as the Larmor frequency $\omega_0$ given by $$\omega_0 = \gamma B_0 \quad (2)$$

where $B_0$ is the static field strength. At the same time, the magnetization returns to the equilibrium direction (i.e., aligned with the static field) according to a decay time known as the "spin-lattice relaxation time" or $T_1$. For hydrogen nuclei $\gamma/2\pi = 4258$ Hz/Gauss, so that a static field of 235 Gauss, would produce a precession frequency of 1 MHz. $T_1$ is controlled by the molecular environment and is typically ten to one thousand ms in rocks.

At the end of a θ=90° tipping pulse, spins on resonance are pointed in a common direction perpendicular to the static field, and they precess at the Larmor frequency. However, because of inhomogeneity in the static field due to the constraints on tool shape, imperfect instrumentation, or microscopic material heterogeneities, each nuclear spin precesses at a slightly different rate. Hence, after a time long compared to the precession period, but shorter than $T_1$, the spins will no longer be precessing in phase. A little over-simplified we can say that this de-phasing occurs with a time constant that is commonly referred to as $T_2^*$ if it is predominantly due to the static field inhomogeneity of the apparatus, and as $T_2$ if it is due to properties of the material.

The receiving coil is designed so that a voltage is induced by the precessing spins. Only that component of the nuclear magnetization that is precessing in the plane perpendicular to the static field is sensed by the coil. After a 180° tipping pulse (an "inversion pulse"), the spins on resonance are aligned opposite to the static field and the magnetization relaxes along the static field axis to the equilibrium direction. Hence, a signal will be generated after a 90° tipping pulse, but not after a 180° tipping pulse in a generally uniform magnetic field.

While many different methods for measuring $T_1$ have been developed, a single standard known as the CPMG sequence (Carr-Purcell-Meiboom-Gill) for measuring $T_2$ has evolved. In contrast to laboratory NMR magnets, well logging tools have inhomogeneous magnetic fields due to the constraints on placing the magnets within a tubular tool and the inherent "inside-out" geometry. Maxwell's divergence theorem dictates that there cannot be a region of high homogeneity outside the tool. Therefore in typical well bores, $T_2^* \ll T_2$, and the free induction decay becomes a measurement of the apparatus-induced inhomogeneities. To measure the true $T_2$ in such situations, it is necessary to cancel the effect of the apparatus-induced inhomogeneities. To accomplish the same, a series of pulses is applied to repeatedly refocus the spin system, canceling the $T_2^*$ effects and forming a series of spin echoes. The decay of echo amplitude is a true measure of the decay due to material properties. Furthermore it can be shown that the decay is in fact composed of a number of different decay components forming a $T_2$ distribution. The echo decay data can be processed to reveal this spectrum which is related to rock pore size distribution and other parameters of interest to the well log analyst.

U.S. Pat. No. 5,023,551 issued to Kleinberg discloses an NMR pulse sequence for use in the borehole environment which combines a modified fast inversion recovery (FIR) pulse sequence with a series of more than ten, and typically hundreds, of CPMG pulses according to $$[W_i - 180_x - t_i - 90_x - (t_{cp} - 180_y - t_{cp} - \text{echo})_j]_i \quad (3)$$

where j=1, 2, ..., J, and J is the number of echoes collected in a single CPMG sequence, where i=1, 2, ..., I and I is the number of waiting times used in the pulse sequence, where $W_i$ are the recovery times before the inversion pulse, and where $t_i$ are the recovery times before a CPMG sequence, and where $t_{CP}$ is the Carr-Purcell spacing. The phase of the RF pulses 90 and 180 is denoted by the subscripts X and Y, Y being phase shifted by $\pi/2$ radians with respect to X. The subscripts also conventionally relate to the axis about which rotation of the magnetization occurs during the RF pulse in a local Cartesian coordinate system centered on the nucleus in which the static magnetic field is aligned in the Z direction and the RF field in the X direction. This sequence can be used to measure both T1 and T2, but is very time consuming, limiting logging speed. If $t_{CP}$ is set to zero and the inverting pulse is omitted then the sequence defaults to standard CPMG for measuring T2 only.

U.S. Pat. No. 6,466,013 to Hawkes et al., and U.S. Pat. No. 6,163,153 to Reiderman et al. teach use of a modified CPMG sequence in which the refocusing pulses have a tipping angle less than 180°. With such a modified CPMG sequence, power usage is reduced without a significant reduction in the signal to noise ratio (SNR).

Tool motion can seriously affect the performance of NMR tools used in an MWD environment. NMR tools that have static and magnetic fields that have complete rotational symmetry are unaffected by rotation of the tool since the fields in the region of examination do not change during the measurement sequence. However, any radial or vertical component of tool motion due to vibration will affect the NMR signal. U.S. Pat. No. 5,389,877 issued to Sezginer describes a truncated CPMG sequence in which the sequence duration and recovery delay are so short that only signals from the clay and capillary bound fluids are detected. A truncated sequence has the advantage that the effect of tool motion on the measurements is reduced due to the short measurement time (approx. 50 ms, compared to greater than 300 ms for normal downhole CPMG measurements.) As discussed in U.S. Pat. No. 5,705,927 issued to Kleinberg, resonance regions of many prior art instruments are of the order of 1 mm. Accordingly, a lateral vibration at a frequency of 50 Hz having an amplitude of 1 mm (10 g acceleration) would disable the instrument. The Kleinberg '927 patent discloses making the length of each CPMG sequence small, e.g. 10 ms, so that for small acceleration the drill collar cannot be displaced by a significant fraction of the vertical or radial extent of the sensitive region during a CPMG pulse sequence. However, as noted above, using such short sequences and short wait times only gives an indication of the bound fluid volume and gives no indication of the total fluid volume.

U.S. Pat. No. 6,268,726 to Prammer et al., teaches the use of motion sensors on a MWD apparatus that makes measurements of tool motion of a NMR sensor assembly. Measurements are made by the NMR sensor during continued drilling operations, and subsequently, the measurements made by the motion sensor are used to select a subset of the NMR measurements that meet certain requirements on tool motion and hence would be expected to give a reasonable insensitivity to tool motion. U.S. Pat. No. 6,459,263 to Hawkes et al., having the same assignee as the present application and the contents of which are fully incorporated herein by reference, uses the output of motion sensors in combination with predictive filtering to control the timing of pulses for a modified (as in the Hawkes '013 patent) or conventional CPMG sequence. One drawback of the Hawkes '263 teaching is that merely changing the pulse timing does not fully compensate for the tool motion.

U.S. Pat. No. 6,566,874 to Speier et al. addresses the problem of tool motion and teaches several approaches to deal with the problem. In one embodiment, measurements are made of two different echo trains that have different sensitivities to tool motion. The tool has two different regions of examination: a high gradient zone defined by one set of magnets and antennas, and a low gradient zone defined by another set of magnets and antennas. The effect of tool motion on the signal amplitude is greater in the high gradient zone than in the low gradient zone. Using these two sets of signals and knowing the gradients of the respective zones, it is possible to estimate what the signal would have been without the tool motion. The patent also teaches that sensitivity to motion may be varied by different field geometries with different gradients. This requirement of having two different regions of examination complicates the hardware. Another drawback (noted in Speier) to the above-described techniques is that the measurements must be separated in time and/or space. In order to interpret the results it is be assumed that, in the absence of motion, the NMR signal (and therefore the formation measured) is the same in both measurements. For a continuously moving logging tool, this condition is not always given. Also the motion during the two measurements should be the same, or at least have the same characteristics.

In another embodiment taught by Speier, measurements are processed to obtain both the $T_1$ and $T_2$ distribution. The effect of tool motion is different on the two types of measurements. This approach has at least two drawbacks. The first is that $T_1$ determination is time consuming. A second drawback is that in the absence of an exact knowledge of the ratio of $T_1/T_2$, the method can only be used for quality control and not for determining both the $T_1$ and $T_2$ distributions.

Another embodiment taught by Speier analyzes the signal shape to give an indication of tool motion. Motion is simulated by altering the frequency of the RF signal. In the absence of a frequency shift, the quadrature component of the received echo signal is substantially zero. During a frequency shift of the RF pulse sequence, the quadrature component can be significant. Measurements made by two different filtering techniques are compared. In one, the signal amplitude in the absorptive channel is taken at the echo maximum. This constitutes a broadband but noisy detection filter. In the second method, the normalized sum over all samples of the absorptive signal is determined. By comparing the two measurements, motion effect can be identified.

Another embodiment taught by Speier makes a comparison of measurements made in adjacent regions. The results derived from adjacent regions (by frequency shifting) are compared to give an indication of tool motion between the two acquisitions.

A sixth embodiment of Speier attempts to address the problems caused by tool motion by preconditioning the spins to saturate a large region for a $T_1$ based determination.

While the methods taught by Speier are quite comprehensive, in one aspect the teachings of Speier are incomplete. Specifically, the motion is simulated by altering the frequency of the RF signal. A better understanding of the effects of tool motion can be obtained by actually simulating the NMR signal of the moving tool with known magnetic field geometry. This is what is done in the present invention and leads to additional insights and additional methods of compensating for the effects of tool motion that are applicable to real world situations.

SUMMARY OF THE INVENTION

A first embodiment of the present invention is an apparatus and method of determining a parameter of interest of an earth formation using a nuclear magnetic resonance (NMR) tool conveyed in a borehole in said formation, wherein the NMR tool has a motion relative to the borehole. A plurality of spin echo signals indicative of said parameter of interest are obtained using the NMR tool. Concurrently, a motion sensor is used for making measurements of the tool motion. A processor is used for correcting the spin echo signals based on correction factors corresponding to the tool motion. The correction factors may be derived from a NMR simulation program. The tool motion may be measured using accelerometers, gyroscopes or magnetometers. The processor may be located downhole or at a surface location. The measurements may be made using either a directional NMR sensor or an axisymmetric sensor.

A second embodiment of the invention is a method and apparatus for determining a parameter of interest of an earth formation using a nuclear magnetic resonance (NMR) tool conveyed in a borehole in the earth formation, the NMR tool having a motion relative to the borehole. A directional transmitter-receiver combination is used for making measurements from a selected region of the formation. Measurements are made by a motion sensor of the tool motion. The transmitter applies a pulsed RF signal wherein a parameter of the pulsing is determined from the motion sensor signal. The received signals are processed for obtaining the parameter of interest. The motion sensor may be an accelerometer, gyroscope or magnetometer. One or more of the frequency, time, phase or amplitude of the pulses may be varied based on the motion sensor signal. Signals from different regions of the formation may be combined.

In a third embodiment of the invention, NMR signals from different azimuthal sectors around the borehole are received separately. The sectors are defined so as to have similar field gradients and tool motion relative to the gradient. Each sector signal is processed separately and the resulting partially processed signals are combined. An axisymmetric transmitter in combination with azimuthally selective receivers may be used. A motion sensor may be used and may be an accelerometer, gyroscope, magnetometer or caliper. The partial processing may include amplitude and phase corrections.

BRIEF DESCRIPTION OF THE DRAWINGS

For a detailed understanding of the present invention, references should be made to the following detailed description of the preferred embodiment, taken in conjunction with the accompanying drawings, in which like elements have been given like numerals, wherein.

DETAILED DESCRIPTION OF THE INVENTION

Figure 1:
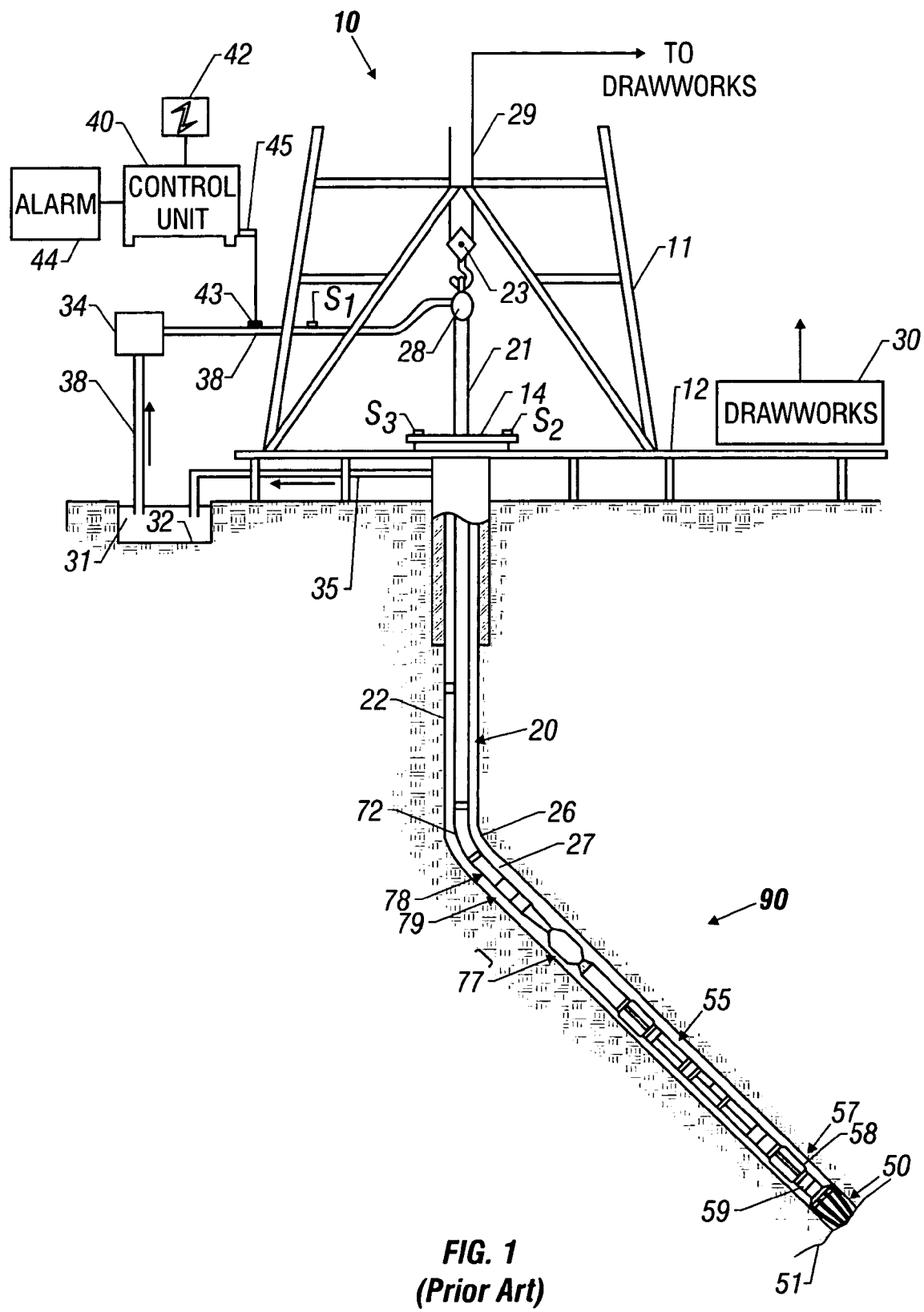
FIG. 1 is a schematic illustration of a drilling system using the present invention.

FIG. 1 shows a schematic diagram of a drilling system 10 with a drillstring 20 carrying a drilling assembly 90 (also referred to as the bottom hole assembly, or "BHA") conveyed in a "wellbore" or "borehole" 26 for drilling the wellbore. The drilling system 10 includes a conventional derrick 11 erected on a floor 12 which supports a rotary table 14 that is rotated by a prime mover such as an electric motor (not shown) at a desired rotational speed. The drillstring 20 includes a tubing such as a drill pipe 22 or a coiled-tubing extending downward from the surface into the borehole 26. The drillstring 20 is pushed into the wellbore 26 when a drill pipe 22 is used as the tubing. For coiled-tubing applications, a tubing injector, such as an injector (not shown), however, is used to move the tubing from a source thereof, such as a reel (not shown), to the wellbore 26. The drill bit 50 attached to the end of the drillstring breaks up the geological formations when it is rotated to drill the borehole 26. If a drill pipe 22 is used, the drillstring 20 is coupled to a drawworks 30 via a Kelly joint 21, swivel, 28 and line 29 through a pulley 23. During drilling operations, the drawworks 30 is operated to control the weight on bit, which is an important parameter that affects the rate of penetration. The operation of the drawworks is well known in the art and is thus not described in detail herein.

During drilling operations, a suitable drilling fluid 31 from a mud pit (source) 32 is circulated under pressure through a channel in the drillstring 20 by a mud pump 34. The drilling fluid passes from the mud pump 34 into the drillstring 20 via a desurger 36, fluid line 28 and Kelly joint 21. The drilling fluid 31 is discharged at the borehole bottom 51 through an opening in the drill bit 50. The drilling fluid 31 circulates uphole through the annular space 27 between the drillstring 20 and the borehole 26 and returns to the mud pit 32 via a return line 35. The drilling fluid acts to lubricate the drill bit 50 and to carry borehole cutting or chips away from the drill bit 50. A sensor $S_1$ preferably placed in the line 38 provides information about the fluid flow rate. A surface torque sensor $S_2$ and a sensor $S_3$ associated with the drillstring 20 respectively provide information about the torque and rotational speed of the drillstring. Additionally, a sensor (not shown) associated with line 29 is used to provide the hook load of the drillstring 20.

In one embodiment of the invention, the drill bit 50 is rotated by only rotating the drill pipe 22. In another embodiment of the invention, a downhole motor 55 (mud motor) is disposed in the drilling assembly 90 to rotate the drill bit 50 and the drill pipe 22 is rotated usually to supplement the rotational power, if required, and to effect changes in the drilling direction.

In the preferred embodiment of FIG. 1, the mud motor 55 is coupled to the drill bit 50 via a drive shaft (not shown)

disposed in a bearing assembly 57. The mud motor rotates the drill bit 50 when the drilling fluid 31 passes through the mud motor 55 under pressure. The bearing assembly 57 supports the radial and axial forces of the drill bit. A stabilizer 58 coupled to the bearing assembly 57 acts as a centralizer for the lowermost portion of the mud motor assembly.

In one embodiment of the invention, a drilling sensor module 59 is placed near the drill bit 50. The drilling sensor module contains sensors, circuitry and processing software and algorithms relating to the dynamic drilling parameters. Such parameters preferably include bit bounce, stick-slip of the drilling assembly, backward rotation, torque, shocks, borehole and annulus pressure, acceleration measurements and other measurements of the drill bit condition. A suitable telemetry or communication sub 72 using, for example, two-way telemetry, is also provided as illustrated in the drilling assembly 100. The drilling sensor module processes the sensor information and transmits it to the surface control unit 40 via the telemetry system 72.

The communication sub 72, a power unit 78 and an MWD tool 79 are all connected in tandem with the drillstring 20. Flex subs, for example, are used in connecting the MWD tool 79 in the drilling assembly 90. Such subs and tools form the bottom hole drilling assembly 90 between the drillstring 20 and the drill bit 50. The drilling assembly 90 makes various measurements including the pulsed nuclear magnetic resonance measurements while the borehole 26 is being drilled. The communication sub 72 obtains the signals and measurements and transfers the signals, using two-way telemetry, for example, to be processed on the surface. Alternatively, the signals can be processed using a downhole processor in the drilling assembly 90.

The surface control unit or processor 40 also receives signals from other downhole sensors and devices and signals from sensors $S_1$-$S_3$ and other sensors used in the system 10 and processes such signals according to programmed instructions provided to the surface control unit 40. The surface control unit 40 displays desired drilling parameters and other information on a display/monitor 42 utilized by an operator to control the drilling operations. The surface control unit 40 preferably includes a computer or a microprocessor-based processing system, memory for storing programs or models and data, a recorder for recording data, and other peripherals. The control unit 40 is preferably adapted to activate alarms 44 when certain unsafe or undesirable operating conditions occur.

Figure 2:
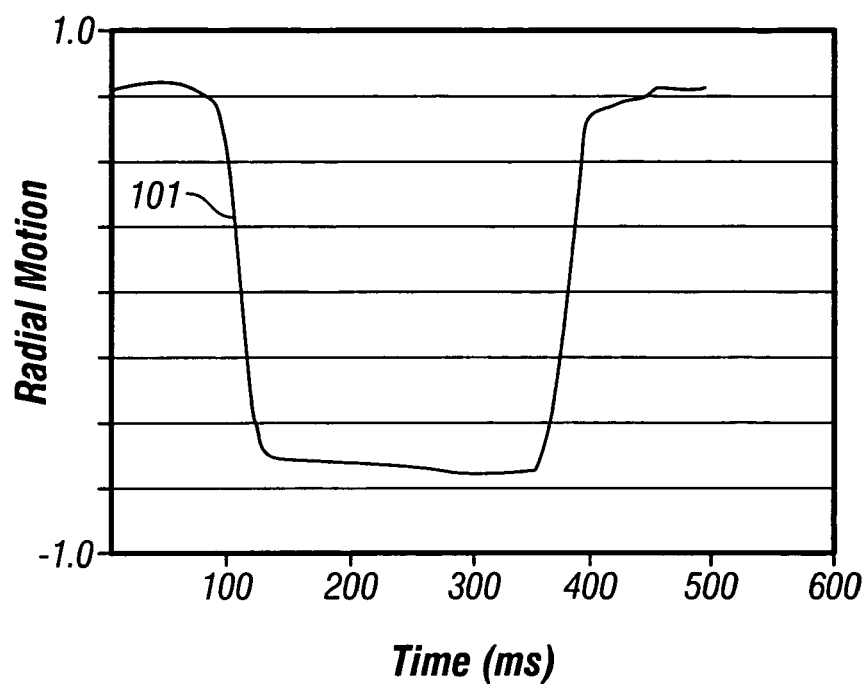
FIG. 2 shows an example of motion applied to an exemplary NMR logging tool.

Prior to discussing the specific aspects of apparatus and method of the present invention for compensating for the effects of tool motion, it is helpful to see exactly what the effects of tool motion are. FIG. 2 shows an example of tool motion that was used in a simulator for an exemplary NMR tool. The magnet configuration comprised two opposed magnets (such as that disclosed in U.S. Pat. No. 4,350,955 to Jackson) having a region of examination midway between magnet poles. The static field gradient is axisymmetric but the antenna was directional, limiting the received signals to an azimuthal sector. The tool was thus a sidelooking NMR tool and the observations are specific to such a tool for reasons discussed below. A radial displacement as indicated by 101 was applied to the tool. The abscissa is time in milliseconds and the ordinate is the displacement in arbitrary units. For the first 100 ms or so, the tool was displaced in one direction from the center of the borehole by 0.75 units. The tool was then moved rapidly 1.5 units in the opposite direction and kept there for 300 ms, and then moved back to the original position.

Figure 3A:
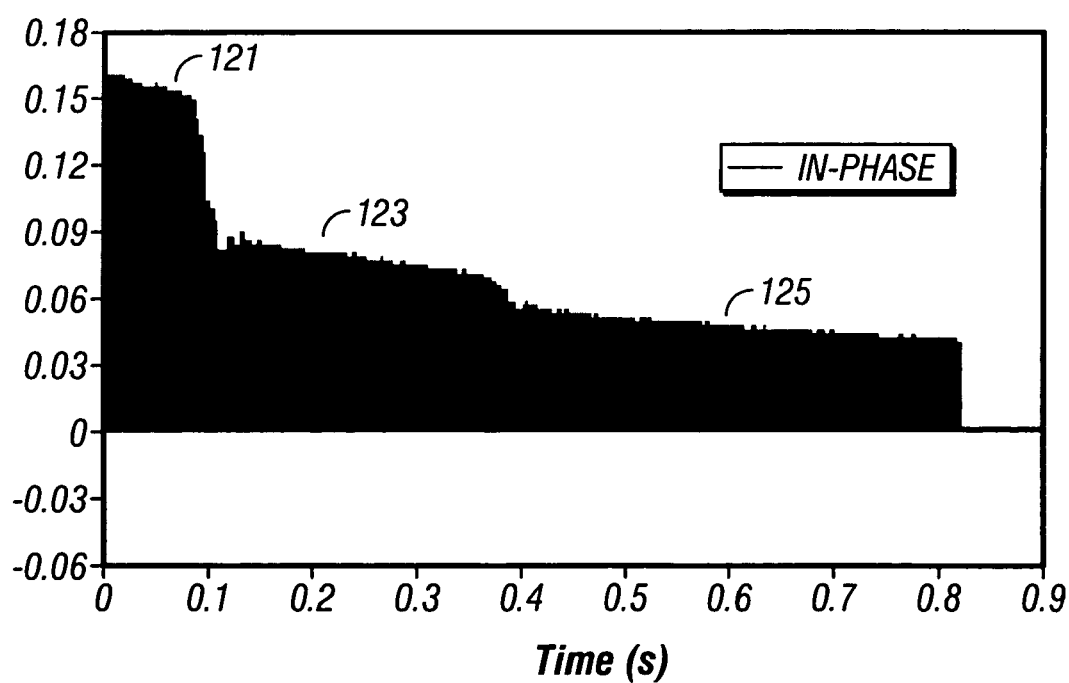
FIGS. 3a and 3b show in-phase (3a) and quadrature (3b) component spin echo signals received by the NMR logging tool when a radio frequency pulse sequence is applied during the tool motion of FIG. 2.
Figure 3B:
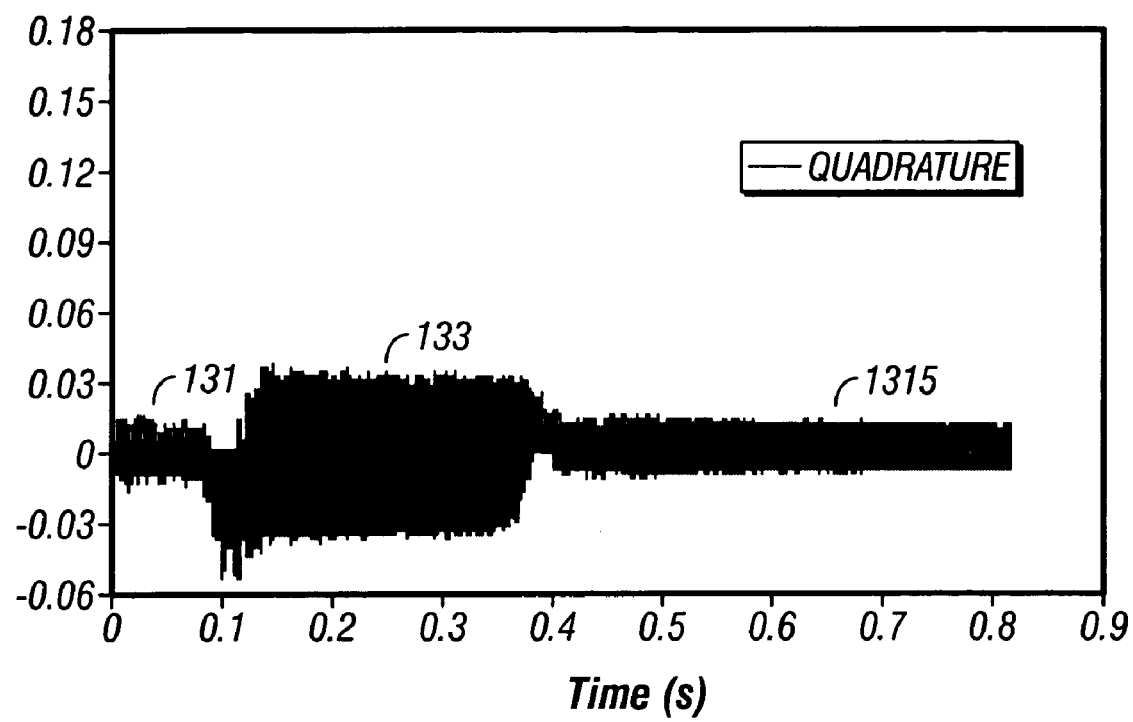

The exemplary NMR tool was pulsed with a pulse sequence consisting of an excitation pulse and a plurality of refocusing pulses during the tool motion shown in FIG. 2. The results are shown in FIGS. 3*a* and 3*b*. Shown are in FIG. 3*a* the in-phase (121, 123, 125) and in FIG. 3*b* the quadrature (131, 133, 133) components of the spin echo signals. As can be seen in FIG. 3*a*, during times when the tool is substantially stationary (seen after 0.5 seconds), the echo in-phase component decays with a $T_2$. The fastest loss of the in-phase component is during rapid movement (around 0.1 s and 0.4 s). The quadrature component in FIG. 3*b* is relatively small before 0.1 s and after 0.5 s (corresponding to times when the tool is in the same position as when the excitation pulse is applied). The quadrature component is larger when the tool is in a position different from where it was at the time of application of the excitation pulse (approximately 0.1-0.5 s). This would correspond to the times when nuclear spins that were tipped by the excitation pulse are in the largest change in the static magnetic field. The quadrature component shows the most rapid change when the tool is in motion. It should be pointed out that only with a side-looking antenna the quadrature component would show features as in this FIG. 3*b*. If signals are acquired with one antenna having an axisymetric tool quadrature components of opposing sides would be about reverse to each other and therefore would be averaged out, resulting in a zero quadrature component. At this point, it is worth emphasizing the differences in simulation here and in the Speier patent. Speier uses frequency changes to simulate tool motion. In contrast, the present simulation uses actual tool motion (in a specific magnetic field configuration) to see what the effect on characteristics of the received signals would be.

Figure 4:
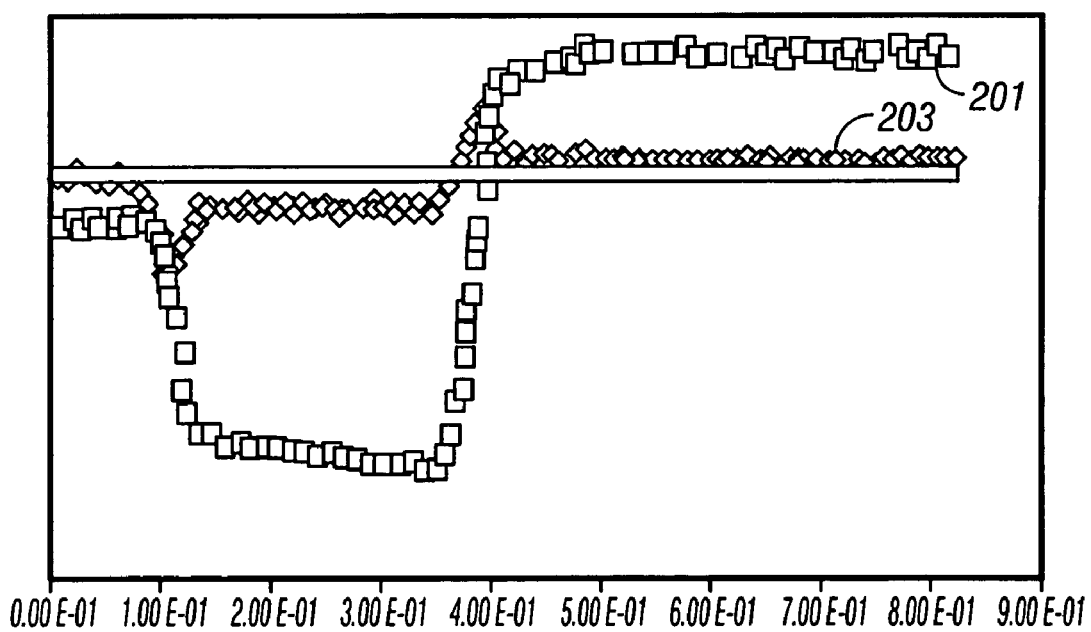
FIG. 4 shows the phases of the spin echo signals corresponding to the in-phase and quadrature components shown in FIG. 3.

Turning now to FIG. 4, the average phase of each echo 201 and phase change over the width of each echo 203 are shown. The average phase seems to be especially sensitive to velocity, while the phase change within the echoes depends mainly on position. The phase change within an echo is equivalent to that echo being off resonance. From the phase change the off resonance frequency can be calculated. The result is shown in FIG. 5.

Figure 5:
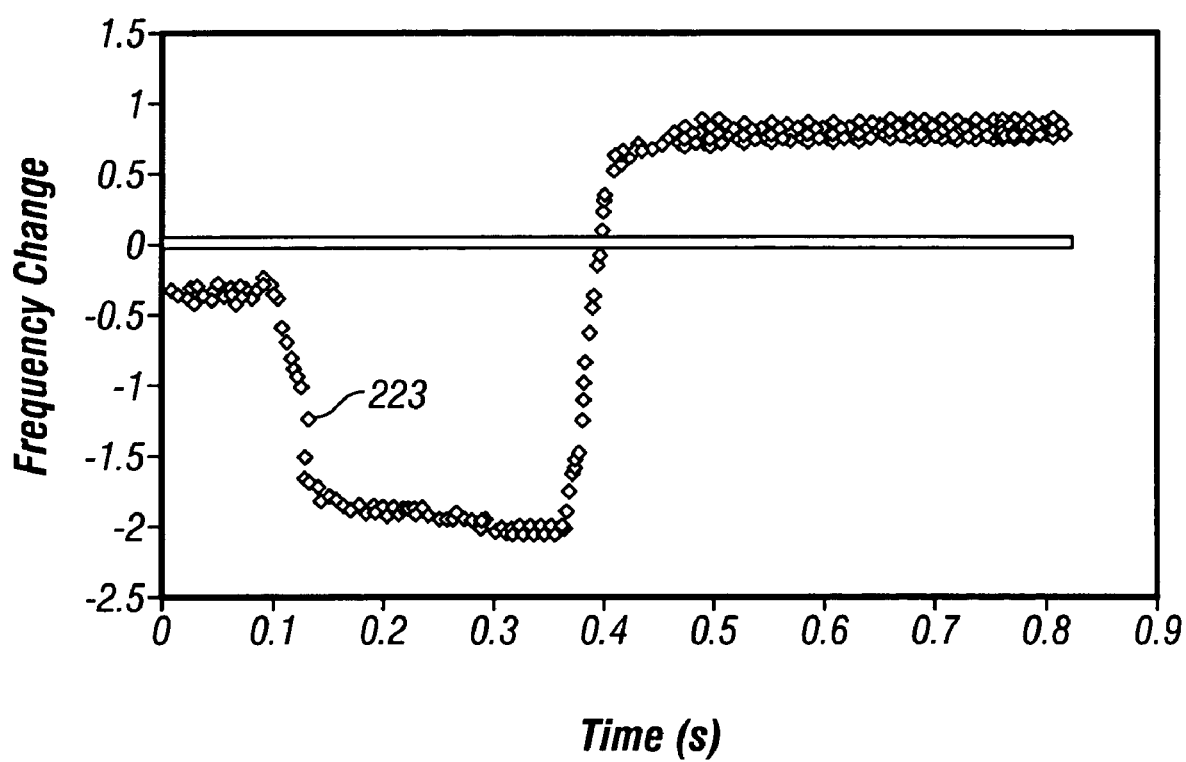
FIG. 5 shows the frequency change corresponding to the tool motion of FIG. 2.

The frequency change is shown in FIG. 5 by 223. As can be seen, between 0.1 s and 0.3 s the frequency change is less than 2 kHz. Comparing this with the traveled distance in FIG. 2, one would expect a shift of 3 kHz for the mid plane between the magnets, and even more away from the mid plane between the two magnets, where the radial gradient increases. The reason that the observed shift is smaller than expected is that because of tool motion, some of the active spins are lost because they became to be positioned outside the RF bandwidth. As a consequence the echo width becomes wider and the amplitude is smaller as described below with reference to FIG. 6. A similar change in frequency happens again at the movement between 0.35 s and 0.4 s, now in the other direction.

Figure 6:
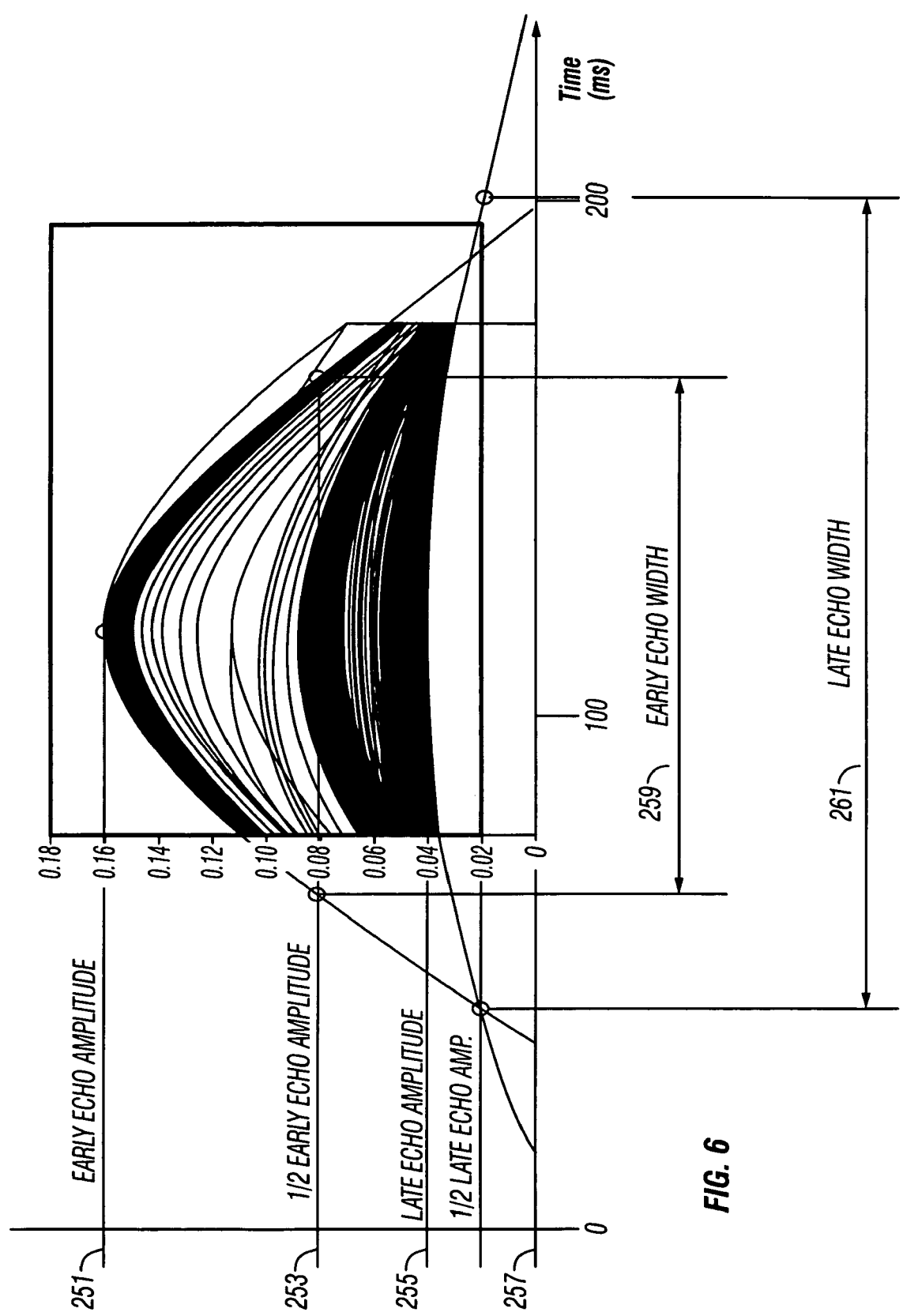
FIG. 6 shows the in phase components of the echos superimposed.

FIG. 6 shows the in-phase components of all the echoes on top of each other. It can be seen that the echoes get wider the lower they become. The early echo amplitudes 251 and half amplitudes 253 are greater than the late echo amplitudes 255 and half amplitudes 257, while the early echo widths 259 are less than the late echo widths 261. The maxima of all the echoes are more or less at the same position between their preceding and succeeding refocusing pulses.

Using the above simulation for guidance, a number of methods have been developed for compensating for the effects of tool motion in an NMR MWD logging system. Some of the methods are based upon segregating the spins into groups that qualitatively sees the same static field change during a motion in order to avoid the cancellation of signals having different signs after being shifted to the quadrature part of the signal. By this, it is meant that spins with positive gradient and motion substantially in the direction of the gradient are in one group, while spins with positive gradient and motion substantially in the opposite direction are in another group. If the NMR tool moves to one side the magnetic field strength may either increase or decrease for the whole group of spins. In this case the movement results in a change of NMR signal phase, change of mid position of the echo or change of signal frequency. These changes can be evaluated to detect and characterize the motion. These methods would not work if the received group of spins includes an ensemble of spins that sees a rise of the static magnetic field and another ensemble of equal number that sees a fall of the static magnetic field for a particular movement. In such a case, all the phase and frequency changes would be averaged to zero. Due to the motion the NMR signal amplitude would decrease, but no indication could be seen in the NMR signal about the motion, because NMR amplitude decrease due to T2 relaxation (wanted) and due to motion (not wanted) could not be distinguished.

A first embodiment of the invention is applicable without having the spins segregated into groups. It takes the measurement of the displacement as an input of the NMR simulation and calculates, based on the knowledge of field geometry and timing between motion and NMR sequence, a characteristic of the motion induced decay. The method then applies this characteristic as a correction for the measured NMR signals.

Figure 10:
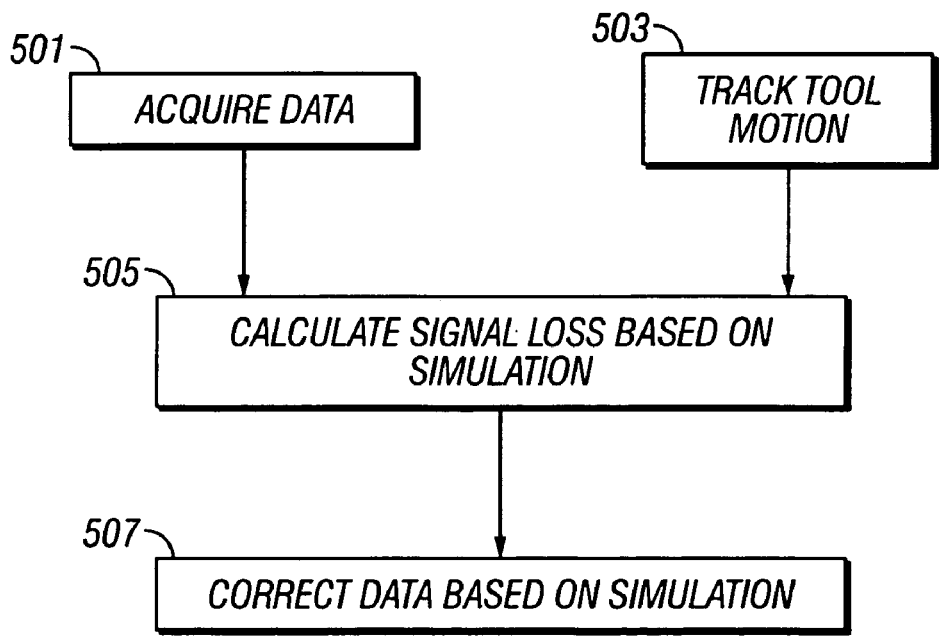
FIG. 10 is a flow chart of the method of an embodiment of the invention.

A flow chart for the first embodiment is given in FIG. 10. An echo train is obtained over the entire volume of investigation 501. This does not require the use of a directional tool. The tool motion is measured concurrently with the NMR data acquisition 503. Based on simulation data, a table of correction factors is derived for each echo 505. As discussed above, the tool motion is preferably derived from measurements with accelerometers, magnetometers, gyroscopes, or callipers. Using the derived correction factors, the echo train is corrected 507. Subsequently, the corrected echo train may be processed using prior art methods to determine parameters of interest such as porosity, bound water irreducible, bound water movable etc.

The correction described at 505 and 507 may be done downhole or at a surface location. The motion is described in an input file to the NMR simulation program. Other inputs to the NMR simulation program are maps of the static and radiofrequency fields and the radiofrequency pulse sequence. The output of the NMR simulation program delivers a simulated sequence of echoes, affected only by tool motion, not by NMR relaxation effects. By dividing the measured echo amplitudes by those of the simulation a corrected echo decay is obtained. Inversion of the latter results in the correct T2 distribution.

A second embodiment of the invention uses a side-looking transmitter and a side-looking receiver. Due to tool motion and the corresponding magnetic field variation at the position of the nuclear spins, the spins originally excited by the first RF pulse of the pulse sequence change their NMR resonance frequency and phase. By following these changes with the transmitting frequency and transmitting phase the signal decay due to motion can be significantly alleviated. Of somewhat lesser importance is the adjustment of the amplitude of the pulse. In this respect, the second embodiment is different from the teachings of Hawkes wherein only the time of the transmitter pulse is altered in response to the tool motion.

A precondition for using this second method is that the static field distribution and the motion track are known. This requires that the motion track must be derived in real time. Tool motion may be obtained by using 3-component accelerometers and performing an integration (to measure velocity) and double integration (to get a tool position). The segregation into groups for compensating for tool motion then comprises partitioning the spin echo signals into groups having similar motion into the direction of static magnetic field gradient. The accelerometers may be disposed on the tool at any convenient location near the NMR antenna. The actual radial displacement and tool azimuth may be obtained using the method disclosed in U.S. patent application Ser. No. 10/654,410 of Macpherson, having the same assignee as the present invention and the contents of which are fully incorporated herein by reference. Other motion sensing devices, such as magnetometers, gyroscopes, calipers or standoff sensors may also be used. A particular case of a standoff sensor is an acoustic standoff sensor.

Figure 8:
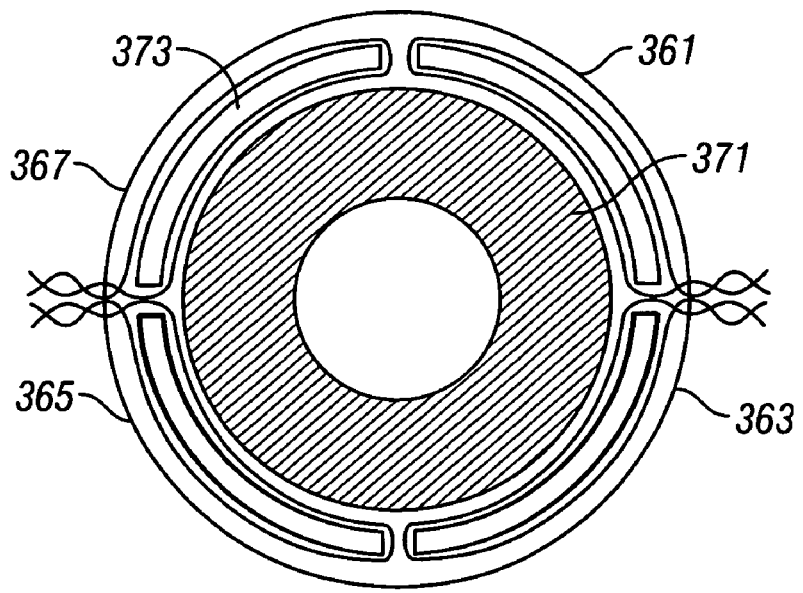
FIG. 8 is a schematic illustration of a directional transmitter-receiver arrangement in an embodiment of the invention.

A variety of side-looking antennas can be used. Here it is important that not only the receiving but also the transmitting antenna be segmented. This is because each group of nuclear spins, which sees different static magnetic field variations, needs different transmit pulses. Such an antenna arrangement is shown in FIG. 8. Shown therein is a tool body 371, one of the antenna cores 373, and four segmented transmitter-receiver combinations 361, 363, 365 and 367.

Figure 9:
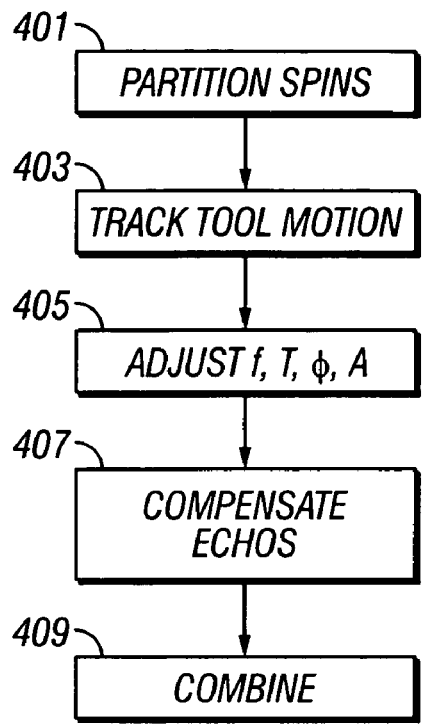
FIG. 9 is a flow chart of the method of an embodiment of the invention.

Implementation of this method is described with reference to FIG. 9. The spins are partitioned into groups of spins, each of which has a similar field gradient and similar motion in the tool coordinate system 401. For example, for the four sectors, with arbitrary tool motion in the x-y-plane, all spins in one sector either move out of the field, into the field, or are not much effected at the same time. The motion should always be defined with respect to the gradient. There should be no possibility of an increase and decrease of the magnetic field at the same time in one sector with arbitrary motion. The tool motion is tracked, e.g., by using accelerometers or other motion sensors 403. Based on the tool motion and the simulation results, the phase and frequency of each transmitted pulse as calculated from the motion data are adjusted 405. Optionally, the start time and amplitude of the transmitter pulses are also adjusted. The NMR echoes of all groups are adjusted 407. This involves adjustment of the phase and frequency of the receiver for each individual echo and each individual group. Optionally, the start time of the acquisition windows may also be adjusted. The adjusted signals of all groups are combined together 409. The combined signal is then processed using prior art methods to obtain parameters of interest of the earth formation, such as porosity, bound volume irreducible or bound water movable.

In a variant of the second embodiment, the transmitter phase for each segment is adjusted for every individual RF pulse to match the actual magnetisation phase which can be calculated real time from the measured motion data. Real time processing and adjustment of the pulse sequence is essential to do this. The times of appearance of the individual echoes and the optimum start times of the RF pulses depend also on the field gradient that is generally motion dependant. Hence in a second variant of the second embodiment, the echo acquisition window and the start times of pulses are adjusted in real time according to the measured motion data. Again, real time processing and adjustment of the pulse sequence is important.

In a third embodiment the NMR signal phase of a side-looking receiving antenna is used to get information about the tool motion. For this purpose one or more side-looking receiving antennas are used. Correcting of motion effects does not simply mean that for each echo and each side-looking receiver an individual phase correction is to be done. After such a phase correction there would still be considerable signal loss. Rather, the phase and frequency information extracted from each (side-looking) echo is used to get information about the motion and is used to correct the signal amplitude accordingly. The processing and correction of the NMR signals according to this invention can be done downhole or uphole.

Figure 7:
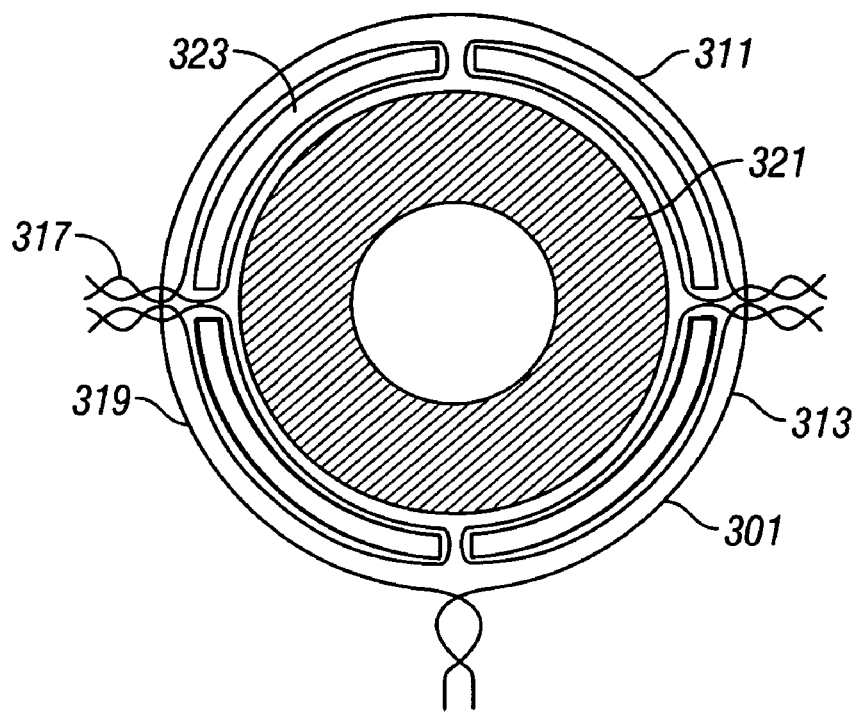
FIG. 7 is a schematic illustration of an axisymmetric transmitter in combination with directional receivers in an embodiment of the invention.

Instead of a side-looking tool with just one receiving antenna, a modified axisymmetric tool is used where the single axisymmetric receiving antenna has been replaced by an azimuthal antenna, i.e. a number of side-looking receiver antennas around the circumference of the tool. This is shown in FIG. 7. Shown therein is the tool body 321, a single axisymmetric transmitter antenna 301 and four segmented receiver antennas denoted by 313, 315, 317 and 319. After the correction the signals of all receiving antennas can be accumulated to increase the signal-to-noise ratio. Even if there are a number of receiving antennas, only one transmitting antenna is needed. In FIG. 7, four receiver antennas are shown. This is not to be construed as a limitation as more segmented antennas may be used. With increasing number of segments, the motion seen by the spins contributing to the signal at a single antenna becomes more uniform; however, the total signal strength decreases. Also shown in FIG. 7 are antenna cores, one of which is denoted by 323. This may be made of a soft magnetic material such as that disclosed in U.S. Pat. No. 6,452,388 of Reiderman et al., or in U.S. patent application Ser. No. 10/177,618 of Kruspe et al., both of which have the same assignee as the present invention and the contents of which are fully incorporated herein by reference.

Once the signals have been corrected, prior art methods can be used to determine parameters of interest of the earth formation and fluids therein. These include clay-bound water (CBW), bound water moveable (BVM), bound water irreducible (BVI), and porosity. Such techniques are well known and are not discussed further herein. It is known in the art that these parameters are estimated from NMR measurements and are not precisely determinable to infinite accuracy. The term "determine" is to be interpreted as being equivalent to "estimate."

It should further be noted that the three embodiments described above are not necessarily limited to independent application. Any combination of the three methods in any order may be used without detracting from the invention.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A method of determining a parameter of interest of an earth formation using a nuclear magnetic resonance (NMR) tool conveyed in a borehole in said formation, said NMR tool having a motion relative to the borehole, the method comprising:
    (a) obtaining at least one NMR signal indicative of the parameter of interest using the NMR tool;
    (b) using a motion sensor for making measurements of the tool motion concurrently with the obtaining of the at least one NMR signal by the NMR tool; and
    (c) correcting the at least one NMR signal based on a predetermined correction factor corresponding to the measurements of tool motion.

2. The method of claim 1 wherein the at least one NMR signal comprises a spin echo signal.

3. The method of claim 1 further comprising determining the correction factor using a NMR simulation program.

4. The method of claim 1 wherein obtaining the at least one NMR signal further comprises:
    (i) polarizing nuclear spins within a region of interest in the earth formation;
    (ii) applying a radio frequency (RF) pulse sequence to the nuclear spins for producing the spin echo signals; and
    (iii) receiving the at least one NMR signal.

5. The method of claim 1 wherein making measurements of the tool motion further comprises using a motion sensor selected from the group consisting of (i) an accelerometer, (ii) a magnetometer, (iii) a gyroscope, (iv) a stand-off measurement, and (v) a caliper.

6. The method of claim 1 wherein correcting the at least one NMR signal further comprises using a processor at a downhole location.

7. The method of claim 1 wherein correcting the at least one NMR signal further comprises using a processor at a surface location.

8. The method of claim 1 wherein the at least one NMR signal comprises an in-phase component and a quadrature component, and processing the at least one NMR signal further comprises applying an amplitude correction and a phase correction to the signal.

9. The method of claim 1 wherein the parameter of interest is selected from the group consisting of (i) clay-bound water (CBW), (ii) bound water moveable (BVM), (iii) bound water irreducible (BVI), and, (iv) porosity.

10. A method of determining a parameter of interest of an earth formation using a nuclear magnetic resonance (NMR) tool conveyed in a borehole in said earth formation, the NMR tool having a motion relative to the borehole, the method comprising:
    (a) polarizing nuclear spins within the earth formation;
    (b) applying a radio frequency (RF) pulse sequence to nuclear spins in a selected region of the earth formation where the nuclear spins experience similar magnetic field changes due to the motion, wherein at least one parameter of a selected pulse of the pulse sequence is based at least in part on signals indicative of the motion, the RF pulse sequence generating at least one NMR signal indicative of the parameter of interest;
    (c) receiving the at least one NMR signal, and
    (d) processing the received at least one NMR signal and determining the parameter of interest.

11. The method of claim 10 wherein the at least one NMR signal comprises a spin echo signal.

12. The method of claim 10 wherein the selected region comprises an azimuthal sector with respect to a center of the NMR tool.

13. The method of claim 10 further comprising obtaining the signals indicative of the motion by using a motion sensor selected from (i) an accelerometer, (ii) a magnetometer, (iii) a gyroscope, (iv) a stand-off measurement and, (v) a caliper.

14. The method of claim 10 wherein at least one NMR signal is received primarily from the specified region.

15. The method of claim 10 wherein the at least one parameter of the pulse sequence is selected from (i) a frequency, (ii) a time, (iii) a phase, and, (iv) an amplitude.

16. The method of claim 10 further comprising
(i) repeating (b)-(d) for at least one additional specified region, and
(ii) combining results from the specified region and the at least one additional specified region.

17. The method of claim 10 wherein the parameter of interest is selected from the group consisting of (i) claybound water (CBW), (ii) bound water moveable (BVM), (iii) bound water irreducible (BVI), and, (iv) porosity.

18. A method of determining a parameter of interest of an earth formation using a nuclear magnetic resonance (NMR) tool conveyed in a borehole in said earth formation, the NMR tool having a motion relative to said borehole, the method comprising:
(a) acquiring at least one NMR signal indicative of the parameter of interest, the at least one NMR signal arising substantially from a selected sector of the earth formation having a specified azimuthal relation relative to the NMR tool;
(b) processing the at least one NMR signal to obtain an estimate of the motion of the NMR tool relative to the borehole; and
(c) determining from the at least one NMR signal and the estimate of the motion of the tool the parameter of interest.

19. The method of claim 18 wherein the at least one NMR signal comprises a spin echo signal.

20. The method of claim 18 further comprising repeating (a)-(c) for at least one additional selected sector of the earth formation different from the selected sector.

21. The method of claim 18 wherein acquiring the at least one NMR signal further comprises:
(i) using a magnet on the NMR tool for polarizing nuclear spins within said selected sector;
(ii) using a transmitter on the NMR tool for applying a radio frequency (RF) pulse sequence to the nuclear spins for producing the at least one NMR signal; and
(iii) using at least one receiver on said NMR tool for receiving at least one NMR signal.

22. The method of claim 18 wherein acquiring the at least one NMR signal further comprises using a receiver having a limited azimuthal sensitivity corresponding to the specified azimuthal relation.

23. The method of claim 18 wherein acquiring the at least one NMR signal further comprises using a transmitter having substantially uniform sensitivity at all azimuths.

24. The method of claim 18 further comprising determining the parameter of interest using a downhole processor.

25. The method of claim 18 further comprising determining the parameter of interest using a processor at a surface location.

26. The method of claim 18 further comprising defining the selected sector so that the nuclear spins contained in the selected sector experience similar magnetic field changes due to the motion of the NMR tool.

27. The method of claim 18 wherein the at least one NMR signal from the selected sector comprises an in-phase component and quadrature component, and processing the at least one NMR signal further comprises applying a phase shift to the at least one NMR signal.

28. The method of claim 18 further comprising applying an amplitude correction to at least one NMR signal.

29. The method of claim 26 wherein the at least one NMR signal from the selected sector comprises an in-phase component and quadrature component, and obtaining the estimate of the motion of the tool further comprises determining a motion induced phase shift of the at least one NMR signal.

30. The method of claim 29 further comprising applying a phase correction or amplitude correction to the at least one NMR signal.

31. An apparatus for use in a borehole in an earth formation, comprising:
(a) a magnet on a nuclear magnetic resonance (NMR) tool which is configured to produce a static magnetic field in the earth formation;
(b) an antenna arrangement on the NMR tool configured to pulse to obtain at least one NMR signal indicative of a parameter of interest;
(c) a motion sensor which is configured to make measurements of motion of the NMR tool concurrently with the obtaining of the at least one NMR signal; and
(d) a processor which is configured to correct the at least one NMR signal based on a predetermined correction factor corresponding to the measurements of the motion sensor.

32. The apparatus of claim 31 wherein the at least one NMR signal comprises a spin echo signal.

33. The apparatus of claim 31 wherein the processor is further configured to determine the correction factor using results of a NMR simulation program.

34. The apparatus of claim 31 wherein the motion sensor is selected from the group consisting of (i) an accelerometer, (ii) a magnetometer, (iii) a gyroscope, (iv) a stand-off measurement sensor and (v) a caliper.

35. The apparatus of claim 31 wherein the processor is at one of (i) a downhole location, and, (ii) a surface location.

36. The apparatus of claim 31 wherein the processor is configured to apply at least one of (i) an amplitude correction, and, (ii) a phase correction to the at least one NMR signal.

37. The apparatus of claim 31 wherein the parameter of interest is selected from the group consisting of (i) claybound water (CBW), (ii) bound water moveable (BVM), (iii) bound water irreducible (BVI), and, (iv) porosity.

38. The apparatus of claim 31 wherein the NMR tool is part of a bottomhole assembly (BHA).

39. The apparatus of claim 38 further comprising a drilling tubular which is configured to convey the BHA to a downhole location.

40. An apparatus for use in a borehole in an earth formation, comprising:
(a) a magnet on a nuclear magnetic resonance (NMR) tool that is configured to polarize nuclear spins within the earth formation;
(b) an antenna on the NMR tool that is configured to apply a radio frequency (RF) pulse sequence to nuclear spins in a selected region of the earth formation where the nuclear spins experience similar magnetic field changes due to a motion of the NMR tool, wherein at least one parameter of a selected pulse of the RF pulse sequence is based at least in part on signals indicative of the motion of the NMR tool, the RF pulse sequence configured to generate at least one NMR signal indicative of a parameter of interest of the earth formation;
(c) an antenna on the NMR tool which is configured to receive the at least one NMR signal, and
(d) a processor that is configured to process the received at least one NMR signal and estimate the parameter of interest.

41. The apparatus of claim 40 wherein the at least one NMR signal comprises a spin echo signal.

42. The apparatus of claim 40 wherein the selected region comprises an azimuthal sector with respect to a center of the NMR tool.

43. The apparatus of claim 40 wherein the signals indicative of the motion of the NMR tool are provided by a motion sensor selected from (i) an accelerometer, (ii) a magnetometer, (iii) a gyroscope, (iv) a stand-off measurement sensor and, (v) a caliper.

44. The apparatus of claim 40 wherein the at least one NMR signal is received primarily from the selected region.

45. The apparatus of claim 40 wherein the at least one parameter of the pulse sequence is selected from (i) a frequency, (ii) a time, (iii) a phase, and, (iv) an amplitude.

46. The apparatus of claim 40 wherein (b)-(d) is repeated for at least one additional specified region.

47. The apparatus of claim 40 wherein the parameter of interest is selected from the group consisting of (i) clay-bound water (CBW), (ii) bound water moveable (BVM), (iii) bound water irreducible (BVI), and, (iv) porosity.

48. The apparatus of claim 40 wherein the NMR tool is part of a bottomhole assembly.

49. The apparatus of claim 48 further comprising a drilling tubular which conveys the BHA into the borehole.

50. An apparatus for use in a borehole in an earth formation, comprising
   (a) a nuclear magnetic resonance (NMR) tool that is configured to acquire at least one NMR signal indicative of a parameter of interest of the earth formation, the at least one NMR signal arising substantially from a selected sector of the earth formation having a specified azimuthal relation relative to the NMR tool;
   (b) a processor that is configured to:
      (A) process the at least one NMR signal to obtain an estimate of motion of the NMR tool relative to the borehole, and
      (B) determine from the at least one NMR signal and the estimate of the motion of the tool the parameter of interest.

51. The apparatus of claim 50 wherein the at least one NMR signal comprises a spin echo signal.

52. The apparatus of claim 50 wherein (a)-(b) are repeated for at least one additional selected sector of the earth formation different from the selected sector.

53. The apparatus of claim 50 wherein NMR tool further comprises:
   (i) a magnet on the NMR tool that is configured to polarize nuclear spins within said selected sector;
   (ii) a transmitter on the NMR tool that is configured to apply a radio frequency (RF) pulse sequence to the nuclear spins and to produce the at least one NMR signal; and
   (iii) at least one receiver on the NMR tool that is configured to receive the at least one NMR signal.

54. The apparatus of claim 50 wherein the at least one receiver has a limited azimuthal sensitivity corresponding to the specified azimuthal relation.

55. The apparatus of claim 50 wherein the transmitter has substantially uniform sensitivity at all azimuths.

56. The apparatus of claim 50 wherein the processor is at one of (i) a downhole location, and, (ii) a surface location.

57. The apparatus of claim 50 wherein the nuclear spins contained in the selected region experience similar magnetic field changes due to the motion of the NMR tool.

58. The apparatus of claim 50 wherein the processor is further configured to apply a phase shift to the at least one NMR signal.

59. The apparatus of claim 50 wherein the processor is further configured to apply an amplitude correction to the at least one NMR signal.

60. The apparatus of claim 57 wherein the processor is configured to obtain the estimate of the motion of the NMR tool by determining a phase shift of the at least one NMR signal.

61. The apparatus of claim 60 wherein the processor is further configured to apply a phase correction or amplitude correction to the at least one NMR signal.

62. The apparatus of claim 50 wherein the NMR tool is part of a bottomhole assembly (BHA).

63. The apparatus of claim 62 further comprising a drilling tubular which is configured to convey the BHA into the borehole.

* * * * *